United States Patent [19]

Gomi et al.

[11] Patent Number: 4,774,076

[45] Date of Patent: * Sep. 27, 1988

[54] ORAL COMPOSITION

[75] Inventors: Tetsuo Gomi, Tokyo; Nobuo Suganuma, Funabashi; Kazuo Ishii, Kawaguchi; Hiroshi Sato, Saitama, all of Japan

[73] Assignee: Lion Corporation, Tokyo, Japan

[*] Notice: The portion of the term of this patent subsequent to Mar. 10, 2004 has been disclaimed.

[21] Appl. No.: 934,748

[22] Filed: Nov. 25, 1986

Related U.S. Application Data

[62] Division of Ser. No. 509,668, Jun. 30, 1983, Pat. No. 4,649,044.

[30] Foreign Application Priority Data

Jun. 30, 1982 [JP] Japan ................................. 57-114505

[51] Int. Cl.$^4$ ................................. A61K 7/16
[52] U.S. Cl. ........................................ 424/49; 424/54
[58] Field of Search ............................ 424/48, 49, 54

[56] References Cited

U.S. PATENT DOCUMENTS 4,649,044 3/1987 Gomi et al. ........................... 424/48

Primary Examiner—J. R. Brown
Assistant Examiner—F. T. Moezie
Attorney, Agent, or Firm—Birch, Stewart, Kolasch & Birch

[57] ABSTRACT

In an oral composition comprising an amino compound, for example, tranexamic acid and ε-aminocaproic acid, a flavor, a surface-active agent, water, and optionally, a humectant, a binder, and an abrasive, the flavor is at least partially comprised of an aldehyde flavor compatible with the amino compound.

11 Claims, No Drawings

ORAL COMPOSITION

This application is a divisional of copending application Ser. No. 509,668, filed on June 30, 1983 now U.S. Pat. No. 4,649,044.

BACKGROUND OF THE INVENTION

This invention relates to oral compositions comprising an amino compound, typically, an antiplasmin agent such as tranexamic acid and ε-aminocaproic acid, and a compatible aldehyde flavor.

It is well known in the art to blend an antiplasmin agent such as tranexamic acid and ε-aminocaproic acid in oral compositions. However, the use of an antiplasmin agent introduced a problem of discoloration of oral compositions as disclosed in Japanese Patent Publication No. 55-5484 and U.S. Pat. No. 4,272,513. This discoloration of antiplasmin agent-containing oral compositions is allegedly attributable to reaction of the antiplasmin agent with an aldehyde group in the coexisting flavor. To avoid discoloration, Japanese Patent Publication No. 55-5484 proposes to blend cyclodextrin in antiplasmin agent-containing oral compositions, and U.S. Pat. No. 4,272,513 proposes the use of a flavor substantially free of an aldehyde group.

It was fully anticipated that when antiplasmin agents such as tranexamic acid and ε-aminocaproic acid and other amino compounds were blended in oral compositions, the amino group would react with an aldehyde group in aldehyde type flavors to form a Schiff base which would cause the oral compositions to be colored or discolored. Particularly when either of the amino compound and the aldehyde flavor is an aryl compound, a stable Schiff base would be formed.

Making a number of experiments using various combinations of amino compounds and aldehyde compounds, the inventors have found that while acetaldehyde, cinnamic aldehyde, t-2-hexanal and the like cause amino compound-containing oral compositions to be colored or discolored, there are certain aldehyde flavors which are compatible with amino compounds. That is, amino compound-containing oral compositions are not colored or discolored when particular compatible aldehyde flavors are blended therein. Particularly, although chain hydrocarbon aldehyde flavors having a double bond between the α- and β-positions with respect to the aldehyde group cause coloring or discoloration of amino compound-containing oral compositions, unexpectedly those cyclic aldhyde compounds having the structure

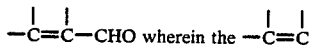

moiety constitutes a segment of the cyclic structure have been found to cause no coloring or discoloration of amino compound-containing oral compositions as long as the compounds are free of a phenolic hydroxyl group. That is, substituted or unsubstituted, phenolic hydroxyl-free cyclic aldehyde compounds having an aldehyde group attached to one of their cyclically concatenating carbon atoms have been found useful as the compatible aldehyde flavors. It has also been found that aliphatic aldehyde compounds having 4 to 7 and 9 to 16 carbon atoms and free of a double bond between the carbon atoms at the α- and β-positions with respect to their aldehyde group are useful as the compatible aldehyde flavors.

SUMMARY OF THE INVENTION

It is, therefore, an object of the present invention to provide an oral composition which comprises an amino compound, but undergoes no coloring or discoloration because the amino acid is combined with a compatible aldehyde flavor.

In an oral composition comprising an amino compound, a flavor, a surface-active agent, water, and optionally, a humectant, a binder, and an abrasive, according to the present invention, the flavor is at least partially comprised of a compatible aldehyde flavor.

In a preferred embodiment of the invention, the compatible aldehyde flavor is selected from substituted and unsubstituted, phenolic hydroxyl-free cyclic aldehyde compounds having an aldehyde group attached to one of their cyclically concatenating carbon atoms. In another preferred embodiment of the invention, the compatible aldehyde flavor is selected from aliphatic aldehyde compounds having 4 to 7 and 9 to 16 carbon atoms and free of a double bond between the carbon atoms at the α- and β-positions with respect to their aldehyde group. Also preferred are aliphatic aldehyde compounds having a double bond between the carbon atoms at the α- and β-positions and a $C_1-C_{12}$ alkyl group or aralkyl group attached at the α-position with respect to their aldehyde group, the total number of carbon atoms of the compounds being 5 to 16.

According to the present invention, by blending compatible aldehyde flavors in amino compound-containing oral compositions, oral compositions with desired flavor are prevented from being colored or discolored without reducing their effectiveness when the amino compound used is an antiplasmin agent. Particularly, when substituted and unsubstituted, phenolic hydroxyl-free cyclic aldehyde compounds (I) having an aldehyde group attached to one of their cyclically concatenating carbon atoms are used as the compatible aldehyde flavor, a choice of the flavor may be made from an increased variety of flavors so that an oral composition capable of imparting pleasant feel when used in the mouth may be readily obtained in spite of the presence of an amino compound which otherwise causes unpleasant feel. When aliphatic aldehyde compounds (II) having 4 to 7 carbon atoms and free of a double bond between the carbon atoms at the α- and β-positions with respect to their aldehyde group are used as the compatible aldehyde flavor, the resulting oral compositions are improved in flavor emission so that they afford improved initial mouth-feel when applied to the mouth. Furthermore, when aliphatic aldehyde compounds (III) having 9 to 16 carbon atoms and free of a double bond between the carbon atoms at the α- and β-positions with respect to their aldehyde group are used as the compatible flavor, the resulting oral compositions are improved in lingering flavor so that they leave an improved aftertaste in the mouth. Aliphatic aldehyde compounds (IV) possessing 5 to 16 carbon atoms in total and having a double bond between the carbon atoms at the α- and β-positions and a $C_1-C_{12}$ alkyl group or aralkyl group attached at the α-position with respect to their aldehyde group are also effective in improving flavor. While it has been a problem that oral compositions having, for example, tranexamic acid blended taste bitter and leave an unpleasant aftertaste in the mouth, the present invention has succeeded in improving the aftertaste of such compositions.

The above and other objects, features and advantages of the present invention will become more apparent and understandable from the following descriptions.

DETAILED DESCRIPTION OF THE INVENTION

The feature of the present invention is to add to an oral composition containing an amino compound an aldehyde flavor which is compatible with the amino compound and does not cause coloring or discoloration of the composition.

The compatible aldehyde flavor may be selected from the aldehyde compounds which are compatible with amino compounds. More particularly, it may be a substituted or unsubstituted, phenolic hydroxyl-free cyclic aldehyde compound (I) having an aldehyde group attached to one of its cyclically concatenating carbon atoms; an aliphatic aldehyde compound (II) having 4 to 7 carbon atoms and free of a double bond between the carbon atoms at the $\alpha$- and $\beta$-positions with respect to its aldehyde group; an aliphatic aldehyde compound (III) having 9 to 16 carbon atoms and free of a double bond between the carbon atoms at the $\alpha$- and $\beta$-positions with respect to its aldehyde group; and an aliphatic aldehyde compound (IV) having a double bond between the carbon atoms at the $\alpha$- and $\beta$-positions and a $C_1$–$C_{12}$ alkyl group or aralkyl group attached at the $\alpha$-position with respect to its aldehyde group, the total number of carbon atoms of the compound being 5 to 16.

The cyclic aldehyde flavors (I) may be either cycloaliphatic or aromatic compounds as long as they have no phenolic hydroxyl group attached to any member of their cyclic structure. Further, the aliphatic compounds may or may not have an unsaturated bond in their cyclic structure. The cyclic aldehyde flavors (I) may also be either unsubstituted cyclic compounds having no substituent other than the aldehyde group and hydrogen atoms attached to the members of their cyclic structure or substituted cyclic compounds having one or more substituents attached to any member of their cyclic structure in addition to the aldehyde group and hydrogen atoms, the substituents being an alkyl group, alkenyl group, alkoxy group and oxygen atom, for example. In the event of cyclic compounds having an unsaturated bond in their cyclic structure, those compounds having an aldehyde group attached to one of the carbon atoms of the unsaturated bond may be used.

Preferred examples of the cyclic aldehyde flavors (I) include benzaldehyde, 2,4-dimethylbenzaldehyde, cuminaldehyde, p-t-butylbenzaldehyde, heliotropin, anisaldehyde, acetylvanillin, 2,4-di-t-butyl-5-methoxybenzaldehyde, 3-t-butyl-4-methoxybenzaldehyde, p-dimethylresorcylic aldehyde, diisopropyldimethylbenzaldehyde, diisopropylmethylbenzaldehyde, p-ethoxybenzaldehyde, tolylaldehyde, ethylbenzaldehyde, 3-methoxy-4-ethoxybenzaldehyde, o-methoxybenzaldehyde, 4-methoxy-3-methylbenzaldehyde, veratraldehyde, myrtenal, dihydromyrtenal, perillaldehyde, 5-(3-buten-2-yl)-3-cyclohexenecarboxylaldehyde, 5-(3-buten-2-yl)-1-methyl-3-cyclohexenecarboxyaldehyde, decahydro-$\beta$-naphthaldehyde, dicyclopentadienaldehyde, 6-methoxydicyclopentadienaldehyde, dihydrocyclocitral, $\alpha$-cyclocitral, $\beta$-cyclocitral, isocyclocitral, dehydro-$\beta$-cyclocitral, 2,4-dimethylcyclohex-3-enaldehyde, 3,4-dimethylcyclohexen-5-ylcarboxyaldehyde, 4-(4-methyl-4-hydroxyamyl)-3-cyclohexenecarboxyaldehyde, 1-methyl-4-(4-methyl-3-pentenyl)-3-cyclohexenecarboxyaldehyde, 4-(4-methyl-3-penten-1-yl)-3-cyclohexane-1-carboxyaldehyde, 4-methylsafranal, phellandral, $\Delta^{2,3}$-2,5,5,9-tetramethyldecalyl-1-ethanal, $\Delta^{1,2}$-2,5,5,9-tetramethyldecalyl-1-ethanal, tetrahydro-p-tolylaldehyde, cyclohexanecarboxyaldehyde, etc. Particularly preferred are perillaldehyde, myrtenal, benzaldehyde, anisaldehyde, and heliotropin. Since such cyclic aldehyde flavors can be used as the compatible flavor in oral compositions containing amino compounds according to the present invention, there are obtained oral compositions presenting more pleasant feel.

The aliphatic aldehyde flavors (II) having 4 to 7 carbon atoms may be either saturated or unsaturated chain compounds which may be of either linear or branched chain and may partially form a cyclic structure. They may be either unsubstituted compounds or substituted compounds having a hydroxyl group, alkoxy group or other groups attached to their skeleton as long as they have 4 to 7 carbon atoms in total and are free of a double bond between the carbon atoms at the $\alpha$- and $\beta$-positions with respect to their aldehyde group.

Examples of the aliphatic aldehyde flavors (II) having 4 to 7 carbon atoms include 3-methylbutanal, 2-methylbutanal, hexanal, heptanal, cis-4-heptenal, trans-4-heptenal, pentanal, 2-ethylbutanal, $\gamma$-hydroxycaproic aldehyde, $\delta$-hydroxyvaleric aldehyde, 3-methylthiopropanal, 2-methyl-propanal, etc. Particularly preferred are 3-methylbutanal, 2-methylbutanal, and hexanal. By using these aliphatic aldehyde flavors having 4 to 7 carbon atoms, amino compound-containing oral compositions display improved flavor emission so that they afford improved initial flavor and pleasant feel in the mouth.

The aliphatic aldehyde flavors (III) having 9 to 16 carbon atoms may also be either saturated or unsaturated chain compounds which may be of either linear or branched chain and may partially form a cyclic structure. They may be either unsubstituted compounds or substituted compounds having a hydroxyl group, alkoxy group or other groups attached to their skeleton as long as they have 9 to 16 carbon atoms in total and are free of a double bond between the carbon atoms at the $\alpha$- and $\beta$-positions with respect to their aldehyde group.

Examples of the aliphatic aldehyde flavors (III) having 9 to 16 carbon atoms include nonanal, decanal, undecanal, dodecanal, tridecanal, tetradecanal, pentadecanal, hexadecanal, 2,6-dimethyl-5-heptenal, 10-undecenal, 2-methylnonanal, 2-methylundecanal, 2-methyldecanal, 2,6-dimethyloctanal, cis-6-nonenal, citronellal, dihydrocitronellal, hydroxycitronellal, methoxycitronellal, isocitronellal, $\beta$-hydroxypelargonic aldehyde, 3-methylnonanal, 2-methyloctanal, 3-methylcitronellal, 3,5,5-trimethylhexanal, n-octyloxyacetaldehyde, decyloxyacetaldehyde, 10,11-dimethyldodecanal, amylheptylacetaldehyde, citronellyloxyacetaldehyde, geranylisobutyraldehyde, geranoxyacetaldehyde, hydroxycitronellyl ethyl carbonate, hexahydrofarnesol, 9-undecenal, cis-8-undecen-1-al, cis-4-undecen-1-al, 3-methyldodecanal, $\alpha$-methyldodecanal, 3-methyltridecanal, 2,6,10-trimethyl-9-undecen-1-al, 2,6,10-trimethylundecanal, decahydro-$\beta$-naphthylacetaldehyde, $\alpha$-ethyl-2,2,6-trimethylcyclohexanebutyric aldehyde, $\beta$-(4-methylcyclohexyl)-butyraldehyde, 2-methyl-4-(2,6,6-trimethyl-1-cyclohexenyl)-3-buten-1-al, 2-methyl-4-(2,6,6-trimethyl-2-cyclohexenyl)-3-buten-1-al, $\beta$-

(4-methyl-3-cyclohexenyl)-butyraldehyde, p-t-amylphenoxyacetaldehyde, m-chlorohydrocinnamic aldehyde, cyclamen aldehyde, p-isobutylhydrocinnamic aldehyde, α-amylhydrocinnamic aldehyde, p-t-butyl-α-methylhydrocinnamic aldehyde, p-ethyl-α,α-dimethylhydrocinnamic aldehyde, α-ethylhydrocinnamic aldehyde, β-benzoxypropionic aldehyde, p-methoxyphenoxyacetaldehyde, α-methylhydrocinnamic aldehyde, p-methylhydrocinnamic aldehyde, 2-methyl-4-phenylbutyraldehyde, 3-methyl-4-phenylvaleric aldehyde, 2-methyl-3-p-tolylpropionaldehyde, α-methyl-3,4-methylenedioxyhydrocinnamic aldehyde, phenetoxyacetaldehyde, 4-phenylbutanal, hydrocinnamic aldehyde, p-isopropylbenzylbutyraldehyde, p-n-propylmethylhydrocinnamic aldehyde, 3-(1-isopropylphenyl)-propionic aldehyde, etc. Particularly preferred are 10-undecenal, decanal, citronellal, and hydroxycitronellal.

The use of these aliphatic aldehyde flavors having 9 to 16 carbon atoms provides a substantial improvement in the lingering flavor of oral compositions containing amino compounds, and particularly, when tranexamic acid is blended in oral compositions, the concomitant bitterness and unpleasant aftertaste are substantially eliminated.

α-methylcinnamaldehyde is a typical example of the aliphatic aldehyde compounds (IV) possessing 5 to 16 carbon atoms in total and having a double bond between the carbon atoms at the α- and β-positions and a $C_1$-$C_{12}$alkyl group or aralkyl group attached at the α-position with respect to their aldehyde group.

In the practice of the invention, the above-mentioned compatible aldehyde flavors may be used alone or in admixture of two or more while combinations of the cyclic aldehyde flavors with the aliphatic aldehyde flavors having 4–7 and 9–16 carbon atoms are preferred because of enhanced pleasant feel. It is to be noted that the compatible aldehyde flavors are usually available as being synthesized or isolated from essential oils. Such synthesized or isolated aldehyde flavors may be blended in oral compositions although the compatible aldehyde flavor may be blended in the form of an essential oil containing it without isolation.

In addition to the compatible aldehyde flavors, the oral compositions of the invention may further contain one or more other flavors, for example, isolated or synthetic flavors such as l-menthol, carvone, anethole, eugenol, cineole, vanillin, zingerone, isoeugenol, guaiacol, creosol, thymol, methyl salicylate, isobutyl salicylate, amyl salicylate, methyl-para-cresol, linalool, etc., and essential oils such as spearmint oil, peppermint oil, anise oil, sage oil, rosemary oil, eucalyptus oil, wintergreen oil, sassafras oil, clove oil, majoram oil, orange oil, strawberry flavor, etc. The presence of the compatible aldehyde flavors allows incompatible aldehyde flavors such as cinnamic aldehyde and salycylic aldehyde to be blended in amino compound containing oral compositions in such an amount that they may not be discolored at all.

In the practice of the invention, a flavor mixture may be previously prepared from two or more of the compatible aldehyde flavors or one or more of the compatible aldehyde flavors and one or more other flavors before it is subsequently blended in oral compositions.

The amount of the compatible aldehyde flavors blended is not particularly limited although it may preferably be blended in an amount of at least 0.01% by weight, especially 0.05 to 90% by weight based on the flavor mixture or the total weight of flavors. In turn, the flavor mixture comprised of the compatible aldehyde flavor may preferably be blended in oral compositions in an amount of 0.01 to 10% by weight, especially 0.05 to 5% by weight of the composition.

According to the present invention, the compatible aldehyde flavors are blended in oral compositions containing amino compounds as described above. As the amino compounds, use may be made of one or more of amino acids, peptides, proteins (including enzymes), amino acid type bactericides, amino acid type surfactants, and antiplasmin agents. Examples of the amino acids include glycine, alanine, β-alanine, glutamic acid, cystine, serine, phenylalanine, etc. Examples of the peptides include caropeptide, glutathione, glycylglycine, aspartylphenylalanyl methyl ester, and peptide type anti-allergy agents. Examples of proteins include gelatin, peptone, albumin, casein, etc. and examples of the enzymes include dextranase, amylase, protease, mutanase, lysozyme and lytic enzyme, etc. Further, examples of the antiplasmin agents include tranexamic acid, ε-aminocaproic acid and their derivatives, for example, alkyl ester derivatives such as hexyl tranexamate, phenyl tranexamate, hexyl ε-aminocaproate, and heptyl ε-aminocaproate, and aryl ester derivatives. Since the use of the compatible aldehyde flavors in combination with the antiplasmin agent prevents the resulting oral compositions from being colored or discolored and improves the unpleasant feel concomitant with the antiplasmin agent, the present invention is particularly advantageously applied to oral compositions containing antiplasmin agents.

The amount of the amino compounds blended varies with their type although they are blended in oral compositions generally in an mount of 0.001 to 10% by weight of the composition. In the case of antiplasmin agents, they are preferably blended in an amount of 0.01 to 5% by weight of the composition.

The oral compositions according to the present invention encompass a variety of oral compositions, for example, dentifrices such as toothpaste, tooth powder and liquid dentifrice, liquid oral refreshers such as mouthwash, solid oral refreshers such as troches, chewing gums, oral pastes and the like. In addition to the above-mentioned ingredients, any suitable ingredients may be selected and blended in the oral compositions of the present invention depending on their type.

More specifically, for dentifrices, abrasives may be blended in an amount of 20–90% by weight (for toothpastes, 20–60% by weight), including dicalcium phosphate dihydrate and anhydride, calcium primary phosphate, calcium tertiary phosphate, calcium carbonate, calcium pyrophosphate, aluminum hydroxide, alumina, silicic anhydride, silica, silica gel, aluminosilicate, aluminum silicate, insoluble sodium metaphosphate, magnesium tertiary phosphate, magnesium carbonate, calcium sulfate, polymethyl methacrylate, bentonite, zirconium silicate, etc. and mixtures thereof.

For pasty compositions, for example, toothpastes, a binder may be blended in an amount of 0.3 to 5% by weight, including synthetic binders such as carrageenan, cellulose derivatives such as sodium carboxymethylcellulose, methyl cellulose, hydroxyethylcellulose, sodium carboxymethylhydroxyethylcellulose, alkali metal alginates such as sodium alginate, propylene glycol alginate, gums such as xanthane gum, tragacanth gum, karaya gum, gum arabic, etc. polyvinyl alcohol, sodium polyacrylate, carboxyvinyl polymer, polyvinyl pyrrolidone, etc. and inorganic binders such as silica gel, aluminum silicate gel, veegum, laponite, etc. and mixtures thereof.

In preparing pasty and liquid oral compositions such as toothpastes and mouthwashes, a humectant may be blended in an amount of 10 to 70% by weight, including sorbitol, glycerine, ethylene glycol, propylene glycol, 1,3-butylene glycol, polyethylene glycol, polypropylene glycol, xylitol, maltitol, lactitol, etc. and mixtures thereof.

Also included are anionic surfactants such as water-soluble salts of higher alkyl sulfates (e.g., sodium lauryl sulfate), sodium salts of higher fatty acids, water-soluble salts of sulfonated monoglycerides of higher fatty acids having 10 to 18 carbon atoms in the fatty acid group (e.g., sodium lauryl monoglyceride sulfonate and sodium coconut monoglyceride sulfonate), higher fatty acid sodium monoglyceride monosulfates, olefin sulfonates, paraffin sulfonates; nonionic surfactants such as fatty acid mono- and di-ethanol amides e.g., lauroyl mono- and di-ethanol amides), stearyl monoglyceride, sucrose fatty acid esters having 12 to 18 carbon atoms in the fatty acid group (e.g., sucrose monolaurate and dilaurate), lactose fatty acid esters, lactitol fatty acid esters, maltitol fatty acid esters, stearic acid monoglyceride, polyoxyethylene sorbitan monolaurate, polyoxyethylene-hardened castor oil, condensates of sorbitan monostearate with approximately 60 moles of ethylene glycol, condensates of ethylene oxide with propylene oxide and their derivatives (e.g., polyoxyethylene polyoxypropylene monolauryl ester), etc.; and amphoteric surfactants such as those of betaine type, etc., alone or in admixture of two or more in an amount of 0 to 10% by weight, preferably 0.1 to 5% by weight.

Also included in the oral compositions according to the present invention are a sweetener such as sodium saccharin, stevioside, neohesperidin dihydrocalcone, glycyrrhizin, perillartine, thaumatin, fractose, sodium cyclaminate, etc. in an amount of 0 to 1% by weight, preferably 0.01 to 0.5% by weight; an antiseptic agent such as p-hydroxymethylbenzoic acid, p-hydroxyethylbenzoic acid, p-hydroxypropylbenzoic acid, p-hydroxybutylbenzoic acid, sodium benzoate, lower fatty acid monoglycerides, etc.; titanium dioxide, ethanol, liquid paraffin, coloring matter, and other additives. For example, toothpastes may be prepared by kneading the desired ingredients selected from the foregoing ingredients with a proper amount of water.

Other types of oral compositions may also be prepared in a conventional manner by selecting commonly used ingredients for the respective types.

In this case, the pH of pasty and liquid oral compositions generally falls in the range of 5 to 10 although not particularly limited thereto.

In the practice of the invention, also blended are one or more active ingredients, for example, alkali metal monofluorophosphates such as sodium monofluorophosphate and potassium monofluorophosphate, fluorides such as sodium fluoride and stannous fluoride, chlorohexidine salts, aluminum chlorohydroxyallantoin, dihydrocholesterol, glycyrrhizin salts, glycyrrhetinic acid, glycerophosphate, chlorophyll, sodium chloride, caropeptide, quaternary ammonium compounds, water-soluble inorganic phosphoric acid compounds, etc.

According to the present invention, by blending a compatible aldehyde flavor in an oral composition containing an amino compound, the resulting oral composition is stable are resistant to discoloration. The blending of the aldehyde flavors imparts to oral compositions pleasant flavor, fine taste and good body as being felt brilliant, sweet or mild. By using the aldehyde flavors alone or in admixture with other flavors, oral compositions containing antiplasmin agents which are previously believed to be unfavorable in flavor and taste can be provided with pleasant feel.

Examples of the present invention are set forth below by way of illustration and not by way of limitation. All percents are by weight.

EXAMPLE 1

Three types of mouthwashes were prepared according to the following formulation: mouthwashes A having aldehyde flavors shown in Table 1 and tranexamic acid, mouthwashes B having the same formulation as mouthwashes A except that tranexamic acid was excluded, and mouthwashes C having the same formulation as mouthwashes A except that the aldehyde flavor was excluded. The tone of the mouthwashes was visually observed both immediately after preparation and after aging at 50° C. for two days, to evaluate their stability. The results are shown in Table 1.

|  | Mouthwash | | |
|---|---|---|---|
| Formulation (% by weight) | A | B | C |
| Tranexamic acid | 0.2 | — | 0.2 |
| Carvone | 0.2 | 0.2 | 0.2 |
| l-Menthol | 0.2 | 0.2 | 0.2 |
| Aldehyde flavor | 0.2 | 0.2 | — |
| Ethanol | 12.0 | 12.0 | 12.0 |
| Polyoxyethylene-hardened castor oil | 4.5 | 4.5 | 4.5 |
| Glycerin | 10.0 | 10.0 | 10.0 |
| Sodium saccharin | 0.5 | 0.5 | 0.5 |
| Water | Balance | Balance | Balance |
|  | 100.0 | 100.0 | 100.0 |

TABLE 1

| Aldehyde flavor | Mouthwash | | | | | |
|---|---|---|---|---|---|---|
|  | A | | B | | C | |
|  | Fresh | Aged | Fresh | Aged | Fresh | Aged |
| 3-Methyl-butanal | — | — | — | — | — | — |
| 2-Methyl-butanal | — | — | — | — | — | — |
| Hexanal | — | — | — | — | — | — |
| Decanal | — | — | — | — | — | — |
| Dodecanal | — | — | — | — | — | — |
| 10-Undecenal | — | — | — | — | — | — |
| Citronellal | — | — | — | — | — | — |
| Hydroxy-citronellal | — | — | — | — | — | — |
| Perillaldehyde | — | — | — | — | — | — |
| Myrtenal | — | — | — | — | — | — |
| Benzaldehyde | — | — | — | — | — | — |
| Anisaldehyde | — | — | — | — | — | — |
| Heliotropin | — | — | — | — | — | — |
| α-Methyl-cinnamaldehyde | — | — | — | — | — | — |
| Acetaldehyde | — | P | — | — | — | — |
| Cinnamic aldehyde | — | Y | — | — | — | — |
| Propanal | — | Y | — | — | — | — |

Note:
— colorless;
P pink;
Y yellow.

As apparent from Table 1, the mouthwashes having acetaldehyde, cinnamic aldehyde and propanal blended with tranexamic acid were discolored whereas the mouthwashes having the remaining aldehyde flavors blended with tranexamic acid were not discolored at all.

For those mouthwashes which contained both the aldehyde flavors and tranexamic acid and had not been discolored, the tranexamic acid was analyzed after two-days aging at 50° C. to find that its content was unchanged, that is, the mouthwashes retained their efficacy.

When 0.76% of sodium monofluorophosphate was further added to the mouthwashes containing both tranexamic acid and the compatible aldehyde flavors, no change of color was observed.

Similar results were obtained when ε-aminocaproic acid was used instead of tranexamic acid.

EXAMPLE 2 Toothpaste

| | |
|---|---|
| Dicalcium phosphate | 50% |
| Silicic anhydride | 2 |
| Propylene glycol | 3 |
| Sorbitol | 10 |
| Glycerin | 10 |
| Sodium saccharin | 0.1 |
| Higher $C_{10}$–$C_{16}$ alcohol lauryl sulfate* | 1.5 |
| Sodium carboxymethyl cellulose | 0.5 |
| Carrageenan | 0.5 |
| Tranexamic acid | 0.1 |
| Flavor mixture No. 1 | 1.0 |
| Water | Balance |
| | 100.0% |

*$C_{10}$ 0–2%, $C_{12}$ 50–80%, $C_{14}$ 10–30%, $C_{16}$ 0–10%

Flavor mixture No. 1 used in this example has the following composition:

| | |
|---|---|
| Carvone | 80% |
| l-Menthol | 14.38 |
| Benzaldehyde | 0.01 |
| Perillaldehyde | 0.01 |
| Coriander oil | 0.1 |
| Orange oil | 0.5 |
| Ethanol | 5 |
| | 100.0% |

EXAMPLE 3 Toothpaste

| | |
|---|---|
| Dicalcium phosphate | 50% |
| Glycerin | 20 |
| Sodium saccharin | 0.1 |
| Perillartine | 0.01 |
| Sodium lauryl sulfate | 2.0 |
| Sodium carboxymethyl cellulose | 1.0 |
| Tranexamic acid | 0.03 |
| Sodium monofluorophosphate | 0.76 |
| Flavor mixture No. 2 | 1.5 |
| Water | Balance |
| | 100.0% |

Flavor mixture No. 2 used in this example has the following composition:

| | |
|---|---|
| Carvone | 40% |
| l-Menthol | 40 |
| Anethole | 8.6 |
| Benzaldehyde | 0.05 |
| Anisaldehyde | 0.03 |
| Decanal | 0.02 |
| Myrtenal | 1.0 |
| Methyl salicylate | 10.0 |
| Sage oil | 0.1 |
| Orange oil | 0.1 |
| Cardamon oil | 0.1 |
| | 100.0% |

EXAMPLE 4 Toothpaste

| | |
|---|---|
| Aluminum hydroxide | 50% |
| Propylene glycol | 2 |
| Sorbitol | 20 |
| Sodium saccharin | 0.05 |
| Sodium lauryl sulfate | 1.2 |
| Sodium carboxymethyl cellulose | 0.8 |
| Carrageenan | 0.3 |
| Tranexamic acid | 0.05 |
| ε-Aminocaproic acid | 0.1 |
| Flavor mixture No. 3 | 0.8 |
| Water | Balance |
| | 100.0% |

Flavor mixture No. 3 used in this example has the following composition:

| | |
|---|---|
| Carvone | 20% |
| l-Menthol | 20 |
| Peppermint oil | 9 |
| Spearmint oil | 20 |
| Anethole | 5 |
| Heliotropin | 0.2 |
| Anisaldehyde | 0.3 |
| Decanal | 0.5 |
| Eugenol | 1 |
| Cineole | 5 |
| Linalool | 5 |
| Ethanol | 14 |
| | 100.0% |

EXAMPLE 5 Toothpaste

| | |
|---|---|
| Aluminum hydroxide | 40% |
| Silicic anhydride | 3 |
| Sorbitol | 5 |
| Glycerin | 20 |
| Sodium saccharin | 0.2 |
| Higher $C_{10}$–$C_{16}$ alcohol lauryl sulfates* | 0.5 |
| Lauroyl diethanol amide | 1.5 |
| Carrageenan | 0.8 |
| Sodium alginate | 0.5 |
| ε-Aminocaproic acid | 1.0 |
| Sodium monofluorophosphate | 0.76 |
| Dextranase ($10^6$ U/g) | 0.2 |
| Gelatin | 0.5 |
| Flavor mixture No. 4 | 1.3 |
| Water | Balance |
| | 100.0% |

*$C_{10}$ 0–2%, $C_{12}$ 50–80%, $C_{14}$ 10–30%, $C_{16}$ 0–10%

Flavor mixture No. 4 used in this example has the following composition:

| | |
|---|---|
| Carvone | 10% |
| l-Menthol | 40 |
| Peppermint oil | 10 |
| Spearmint oil | 33.4 |
| Benzaldehyde | 3 |
| Hexanal | 1 |
| α-methylcinnamaldehyde | 1 |
| Thymol | 0.1 |
| Sage oil | 0.5% |
| Cardamon oil | 1 |

EXAMPLE 6 Toothpaste

| | |
|---|---|
| Dicalcium phosphate | 20% |
| Aluminum hydroxide | 30 |
| Propylene glycol | 1 |
| Sorbitol | 8 |
| Glycerin | 15 |
| Stevioside | 0.1 |
| Sodium lauryl sulfate | 1.0 |
| Carrageenan | 1.0 |
| Tranexamic acid | 0.5 |
| Chlorohexidine hydrochloride | 0.1 |
| Flavor mixture No. 5 | 1.0 |
| Water | Balance |
| | 100.0% |

Flavor mixture No. 5 used in this example has the following composition:

| | |
|---|---|
| Carvone | 20% |
| l-Menthol | 66 |
| 2-Methylbutanal | 2 |
| 3-Methylbutanal | 33 |
| Citronellal | 2 |
| Perillaldehyde | 2 |
| 10-Undecenal | 1 |
| Linalool | 0.5 |
| Orange oil | 0.5% |
| Ethanol | 3 |
| | 100.0% |

EXAMPLE 7 Toothpaste

| | |
|---|---|
| Silicic anhydride | 20% |
| Sorbitol | 20 |
| Glycerin | 40 |
| Sodium saccharin | 0.1 |
| Aspartylphenylallanine methyl ester | 0.01 |
| Sodium lauryl sulfate | 3.0 |
| Sodium alginate | 1.0 |
| ε-Aminocaproic acid | 0.05 |
| Flavor mixture No. 6 | 2.0 |
| Water | Balance |
| | 100.0% |

Flavor mixture No. 6 used in this example has the following composition:

| | |
|---|---|
| Carvone | 30% |
| l-Menthol | 20 |
| Peppermint oil | 20 |
| Benzaldehyde | 8 |
| Decanal | 10 |
| 3-Methylbutanal | 10 |
| Hydroxycitronellal | 1 |
| Myrtenal | 1 |
| | 100.0% |

EXAMPLE 8 Liquid dentifrice

| | |
|---|---|
| Calcium carbonate | 80% |
| Glycerin | 10 |
| Stevioside | 0.01 |
| Perillartine | 0.1 |
| Higher $C_{10}$–$C_{16}$ alcohol lauryl sulfates* | 0.5 |
| Tranexamic acid | 0.1 |
| Aluminum chlorohydroxyallantoinate | 0.1 |
| Dipotassium glycyrrhizin | 0.1 |
| Flavor mixture No. 7 | 0.5 |
| Water | Balance |
| | 100.0% |

*$C_{10}$ 0–2%, $C_{12}$ 50–80%, $C_{14}$ 10–30%, $C_{16}$ 0–10%

Flavor mixture No. 7 used in this example has the following composition:

| | |
|---|---|
| Carvone | 10% |
| l-Menthol | 10 |
| Anisaldehyde | 20 |
| Decanal | 20 |
| 2-Methylbutanal | 20 |
| Perilla oil | 20 |
| | 100.0% |

EXAMPLE 9 Toothpaste

| | |
|---|---|
| Calcium carbonate | 40% |
| Silicic anhydride | 3 |
| Propylene glycol | 3 |
| Sorbitol | 10 |
| Glycerin | 15 |
| Stevioside | 0.1% |
| Sodium lauryl sulfate | 1.5 |
| Sodium carboxymethyl cellulose | 1.0 |
| Tranexamic acid | 2.0 |
| Sodium chloride | 10.0 |
| Flavor mixture No. 8 | 1.2 |
| Water | Balance |
| | 100.0 |

Flavor mixture No. 8 used in this example has the following composition:

| | |
|---|---|
| Carvone | 80% |
| l-Menthol | 8 |
| Benzaldehyde | 5 |
| Anisaldehyde | 1 |
| Decanal | 1 |
| 3-Methylbutanal | 1 |
| Citronellal | 1 |
| Perillaldehyde | 1 |
| Eugenol | 1 |
| Orange oil | 2 |
| | 100.0% |

EXAMPLE 10 Liquid dentifrice

| | |
|---|---|
| Glycerin | 35% |
| Propylene glycol | 5.0 |
| Sodium polyacrylate | 3.0 |
| Sodium lauryl sulfate | 1.0 |
| Sodium saccharin | 0.2 |
| Ethanol | 3.0 |
| Tranexamic acid | 3.0 |
| Flavor mixture No. 9 | 2.0 |
| Water | Balance |
| | 100.0% |

Flavor mixture No. 9 used in this example has the following composition:

| | |
|---|---|
| Carvone | 15% |
| l-Menthol | 40 |

| | |
|---|---|
| Peppermint oil | 20 |
| Spearmint oil | 15 |
| Benzaldehyde | 5 |
| Cineole | 5 |
| | 100.0% |

EXAMPLE 11 Mouthwash

| | |
|---|---|
| Ethanol (90%) | 20% |
| Sodium saccharin | 0.3 |
| Polyoxyethylene-hardened castor oil | 0.5 |
| ε-Aminocaproic acid | 0.05 |
| Flavor mixture No. 10 | 3.0 |
| Water | Balance |
| | 100.0% |

Flavor mixture No. 10 used in this example has the following composition:

| | |
|---|---|
| Carvone | 20% |
| l-Menthol | 50 |
| Anethole | 10 |
| Eugenol | 5 |
| Linalool | 2 |
| Myrtenal | 2 |
| Perillaldehyde | 3 |
| Cineole | 8 |
| | 100.0% |

EXAMPLE 12 Oral paste

| | |
|---|---|
| Liquid paraffin | 26% |
| Sorbitol | 5 |
| Glycerin | 15 |
| Cetanol | 4 |
| Paraffin wax | 6 |
| Microcrystalline wax | 10 |
| Polyoxyethylene sorbitan monooleate | 5 |
| Tranexamic acid | 0.1 |
| Flavor mixture No. 11 | 1.0 |
| Water | Balance |
| | 100.0% |

Flavor mixture No. 11 used in this example has the following composition:

| | |
|---|---|
| Carvone | 10% |
| l-Menthol | 40 |
| Anethole | 5 |
| Peppermint oil | 15 |
| Spearmint oil | 15 |
| Eugenol | 5 |
| Thymol | 5 |
| Perillaldehyde | 2 |
| Hexanal | 2 |
| Citronellal | 1 |
| | 100.0% |

The oral compositions of Examples 2-12 were all resistant to coloring and discoloration and gave pleasant feel when applied to the mouth.

What is claimed is:

1. An oral composition selected from the group consisting of a mouthwash, toothpaste, toothpowder, and liquid dentifrice, comprising:
    an antiplasmin effective amount of an antiplasmin agent selected from the group consisting of tranexamic acid, ε-aminocaproic acid and their water-soluble alkyl ester and aryl ester derivatives,
    a flavor,
    a surface-active agent and water wherein said flavor is at least comprised of a compatible aldehyde flavor selected from the group consisting of substituted and unsubstituted phenolic hydroxyl-free cyclic aldehyde compounds having an aldehyde group attached to one of their cyclically concatenating carbon atoms, aliphatic aldehyde compounds having 4 to 7 carbon atoms and free of a double bond between the carbon atoms at the α- and β-positions with respect to their aldehyde group, aliphatic aldehyde compounds having 9 to 16 carbon atoms and free of a double bond between the carbon atoms at the α- and β-positions with respect to their aldehyde group, and aliphatic aldehyde compounds having 5 to 6 carbon atoms in total having a double bond between the carbon atoms at the α- and β-positions and a $C_1$-$C_{12}$ alkyl group or aralkyl group attached at the α-position with respect to their aldehyde group, and mixtures thereof.

2. The oral composition according to claim 1, wherein said oral composition is a mouthwash.

3. The oral composition according to claim 1, wherein the aldehyde flavor is selected from the group consisting of perillaldehyde, myrtenal, benzaldehyde, anisaldehyde, and heliotropin.

4. The oral composition according to claim 1, wherein the aldehyde flavor is selected from the group consisting of 4-methylbutanal, 2-methylbutanal, and hexanal.

5. The oral composition according to claim 1, wherein the aliphatic aldehyde flavor is selected from the group consisting of 10-undecenal, decanal, citronellal, dodecanal and hydroxycitronellal.

6. The oral composition according to claim 1, wherein the aldehyde flavor is α-methylcinnamaldehyde.

7. An oral composition selected from the group consisting of a mouthwash, toothpaste, toothpowder, and liquid dentifrice, comprising:
    0.01 to 5% by weight of an antiplasmin agent selected from the group consisting of tranexamic acid, ε-aminocaproic acid and their water-soluble alkyl ester and aryl ester derivatives,
    0.01 to 10% by weight of a flavor mixture,
    a surface-active agent and water wherein said flavor mixture comprises 0.05 to 90% by weight based on the total weight of the flavor mixture of a compatible aldehyde flavor selected from the group consisting of substituted and unsubstituted phenolic hydroxyl-free cyclic aldehyde compounds having an aldehyde group attached to one of their cyclically concatenating carbon atoms, aliphatic aldehyde compounds having 4 to 7 carbon atoms and free of a double bond between the carbon atoms at the α- and β-positions with respect to their aldehyde group, aliphatic aldehyde compounds having 9 to 16 carbon atoms and free of a double bond between the carbon atoms at the α- and β-positions with respect to their aldehyde group, and aliphatic aldehyde compounds possessing 5 to 16 carbon atoms in total having a double bond between the carbon atoms at the α- and β-positions and a $C_1$-$C_{12}$ alkyl group or aralkyl group attached at the α-position with respect to their aldehyde group, and mixtures thereof.

8. The oral composition according to claim 7, wherein the aldehyde flavor is selected from the group consisting of perillaldehyde, myrtenal, benzaldehyde, anisaldehyde, and heliotropin.

9. The oral composition according to claim 7, wherein the aldehyde flavor is selected from the group consisting of 3-methylbutanal, 2-methylbutanal, and hexanal.

10. The oral composition according to claim 7, wherein the aliphatic aldehyde flavor is selected from the group consisting of 1-undecenal, decanal, citronellal, dodecanal and hydroxycitronellal.

11. The oral composition according to claim 7, wherein the aldehyde flavor is α-methylcinnamaldehyde.

* * * * *